United States Patent [19]
Ash

[11] Patent Number: 6,156,007
[45] Date of Patent: Dec. 5, 2000

[54] APPARATUS FOR WHOLE-BODY HYPERTHERMIA

[75] Inventor: Stephen R. Ash, Lafayette, Ind.

[73] Assignee: HemoTherm, Inc., West Lafayette, Ind.

[21] Appl. No.: 09/126,372

[22] Filed: Jan. 26, 1995

Related U.S. Application Data

[63] Continuation-in-part of application No. 08/318,132, Oct. 4, 1994, Pat. No. 5,476,444, which is a continuation-in-part of application No. 07/940,646, Sep. 4, 1992, Pat. No. 5,354,277.

[51] Int. Cl.$^7$ .................................................. A61M 1/00
[52] U.S. Cl. ........................... 604/113; 607/96; 607/105; 607/106
[58] Field of Search .................................... 604/113, 4–6; 607/96, 104, 105, 106, 113, 114

[56] References Cited

U.S. PATENT DOCUMENTS

| | | | |
|---|---|---|---|
| 4,908,014 | 3/1990 | Kroyer | 604/113 X |
| 5,277,820 | 1/1994 | Ash | 210/646 |
| 5,354,277 | 10/1994 | Guzman et al. | 604/113 |
| 5,989,238 | 11/1999 | Ginsburg | 604/113 X |

OTHER PUBLICATIONS

Alonso, K., M.D., Pontiggia, P., M.D., Sabato, A., M.D., Calvi, G., M.D., Curto, F.C., M.D., de Bartolomei, E., M.D., Nardi, C., M.D., Cereda, P., M.D., "Systemic Hyperthermia in The Treatment of HIV Related Disseminated Kaposi's Sarcoma. Long–Term Follow–Up Of Patients Treated With Low Flow Extracorporeal Perfusion Hyperthermia", *Eight International San Rocco Cancer Seminar* (Sep. 26, 1992).

Beral, V., Peterman, T.A., Berkelman, R.L., Jaffe, H.W., "Kaposi's Sarcoma Among Persons With AIDS: A Sexually Transmitted Infection?", *The Lancet*, vol. 335, pp. 123–128 (Jan. 20, 1990).

Bull, J.M., M.D., Lees, D., M.D., Schuette, W., Whang–Peng, J., M.D., Smith, R., R.N., Bynum, G., M.D., Atkinson, E.R., Ph.D., Gottdiener, J.S., M.D., Granlick, H.R., M.D., Shawker, T.H., M.D., DeVita, Jr., V.T., M.D., "Whole Body Hyperthermia: A Phase–I Trial Of a Potential Adjuvant To Chemotherapy", *Annals of Internal Medicine*, vol. 90, pp. 317–323 (1979).

Cavaliere, R., M.D., Ciocatto, E.C., M.D., Giovanella, B.C., Ph.D., Heidelberger, C., Ph.D., Johnson, R.O., M.D., Margottini, M., M.D., Mondovi, B., M.D., Moricca, G., M.D., Rossi–Fanelli, A., M.D., "Selective Heat Sensitivity of Cancer Cells", *Cancer*, vol. 20, No. 9, pp. 1351–1381 (Sep.1967).

Hornback, N.B., M.D., "Historical Aspects of Hyperthermia In Cancer Therapy", *Hyperthermia*, vol. 27, No. 3, pp. 481–488 (May 1989).

Larkin, J.M., M.D., Edwards, W.S., M.D., Smith, D.E., M.D., Clark, P.J., M.D., "Systemic Thermotherapy: Description Of a Method And Physiologic Tolerance In Clinical Subjects", *Cancer*, vol. 40, pp. 3155–3159 (Dec. 1977).

(List continued on next page.)

*Primary Examiner*—John B. Yasko
*Attorney, Agent, or Firm*—Woodard, Emhardt, Naughton Moriarty & McNett

[57] ABSTRACT

An apparatus for use in whole body hypothermia includes a dialyzer having a blood side and a dialysate side separated by one or more dialysis membranes. A blood pump associated with the a blood circuit established on the blood side circulates blood through the dialyzer at high rates advantageous for hyperthermia treatments. A bypass is included whereby circulated blood can bypass the dialyzer. The bypass aids in preventing blood-side tensioning of dialyzer membranes thereby allowing proper membrane movement to assist in mixing a sorbent suspension circulated on the dialysate side of the dialyzer. A sorbent suspension composition for use as a dialysate in hemodialysis, especially when performed in conjunction with whole body hyperthermia, includes water, a surface adsorptive agent such as charcoal, a cation exchanger, and precipitated calcium phosphate. The precipitated calcium phosphate serves as a reservoir for calcium and phosphate ions to assist in controlling patient blood chemistries.

10 Claims, 3 Drawing Sheets

OTHER PUBLICATIONS

McDougal, J.S., Martin, L.S., Cort, S.P., Moxen, M., Heldebrant, C.M., Evatt, B.L., "Thermal Inactivation Of The Immunodeficiency Syndrome Virus, Human T Lymphotropic Virus–III/Lymphadenopathy–Associated Virus, With Special Reference to Antihemophilic Factor", *J. Clin. Invest.*, vol. 76, pp. 875–877 (Aug. 1985).

Mondovi, V., Strom, R., Rotilio, G., Agro, A.F., Cavaliere, R., Fanelli, A.R., "The Biochemical Mechanism Of Selective Heat Sensitivity Of Cancer Cells. I. Studies On Cellular Respiration", *Europ. J. Cancer*, vol. 5, pp. 129–136 (1969).

Parks, L.C., M.D., Minaberry, D., R.N., Smith, D.P., M.D., Neey, W.A., M.D., "Treatment Of Far–Advanced Bronchogenic Carcinoma By Extracorporeally Induced Systemic Hyperthermia", *J. Thorac. Cardiovasc. Surg.*, vol. 78, pp. 883–892 (1979).

Robins, H.I., M.D., Ph.D., Hugander, A., M.D., Ph.D., Cohen, J.D., M.D., "Whole Body Hyperthermia In The Treatment Of Neoplastic Disease", *Hyperthermia*, vol. 27, No. 3, pp. 603–610 (May 1989).

Shen, R.–N., Hornback, N.B., Shidnia, H., Lu, L., Broxmeyer, H.E., Brahmi, Z., "Effect Of Whole–Body Hyperthermia And Cyclophosphamide On Natual Killer Cell Activity In Murine Erythroleukemia", *Cancer Research*, vol. 48, pp. 4561–4563 (Aug. 15, 1988).

Spire, B., Dormont, D., Barré–Sinoussi, F., Montagnier, L., Chermann, J.C., "Inactivation Of Lymphadenopathy–Associated Virus By Heat, Gamma Rays, And Ultraviolet Light", *The Lancet*, pp. 188–189 (Jan. 26, 1985).

Yatvin, M.B., "An Approach To AIDS Therapy Using Hyperthermia And Membrane Modification", *Medical Hypotheses*, vol. 27, pp. 163–165 (1988).

Yatvin, M.B., Cramp, W.A., "Role Of Cellular Membranes In Hyperthermia: Some Observations And Theories Reviewed", *Int. J. Hyperthermia*, vol. 9, No. 2, pp. 165–185 (1993).

Yatvin, M.B., Stowell, M.H.B., Steinhart, C.R., "Shedding Light On The Use Of Heat To Treat HIV Infections", *Oncology*, vol, 50, pp. 380–389 (1993).

APPARATUS FOR WHOLE-BODY HYPERTHERMIA

This is a continuation-in-part of U.S. patent application Ser. No. 08/318,132, filed Oct. 4, 1994, now issued as U.S. Pat. No. 5,476,444, which is a continuation-in-part of U.S. patent application Ser. No. 07/940,546 filed Sep. 4, 1992, now issued as U.S. Pat. No. 5,354,227.

FIELD OF THE INVENTION

The present invention relates to a specialized device for whole-body hyperthermia, including extracorporeal blood heating and dialysis, as an antiviral protocol.

BACKGROUND OF THE INVENTION

Whole body hyperthermia (WBHT) as a treatment for neoplasms has been carefully studied and applied since the 1960s (3,4,27). Prior to that period there were multiple reports of tumor regression coincident with induced fever. Biochemical studies of the effects of hyperthermia have indicated that temperatures greater than 41° C. induce necrosis of some types of tumor (3,5). In the body, there are additional physiologic effects by which hyperthermia induces tumor necrosis. In both normal and tumorous tissue, hyperthermia causes an initial vasodilation of blood vessels with a resulting increase in blood flow. Then, there is a decrease in blood flow due to autoregulation and vasoconstriction (6). Tumor tissues have less vascular reactivity to autoregulate blood flow, and are therefore more prone than normal tissues to the effects of high temperature during either local hyperthermia or WBHT (7).

It is now generally accepted that hyperthermia is a useful therapy in treatment of cancers, and regional hyperthermia for accessible tumors is used in every major cancer therapy center in the U.S. Regional hyperthermia is a valuable adjunct to radiation and chemotherapy, because it carries low risk, has few side effects, and often exerts its best effects in patients whose lesions are unresponsive to radiation or chemotherapy (3). In metastatic solid tissue tumors, WBHT is used more than regional hyperthermia, since it is difficult to apply regional therapy to lesions in the abdomen or chest. Even in patients who have failed radiation or chemotherapy, there is a partial remission of the tumors in about half of the patients, and complete remission in a few patients. These results are similar to those obtained with many drugs; however, with drug therapy of cancer, the incidence of side-effects is approximately 100%. Though there are some side-effects of WBHT, most of them are short-lived and not serious.

Kaposi's sarcoma (KS) is the most common neoplasm of patients with AIDS, being seen primarily in the male homosexual AIDS population (8). Unlike the classical KS, the AIDS-related form is often aggressive, presenting with multiple, large cutaneous tumors and early visceral dissemination. The etiology of KS in these patients is uncertain. Cytomegalic viral infections, other sexually transmitted organisms, volatile nitrate inhalation, oncogenes, hormones and HLA type have all been suggested as possible co-factors. KS is currently reported as the primary diagnosis in 13% of hospital admissions of all AIDS patients (9) and the disfiguring disease accounts for substantial morbidity.

Of all tumors, KS seems to be the most sensitive to systemic hyperthermia. In a 1985 survey of 21 patients treated with hyperthermia for cancer, the only patient with complete remission was one with KS (10). According to the investigators, this patient is the only one of the 21 treated who is still alive; the KS lesions have not recurred. A case report in 1990 indicated dramatic resolution of KS lesions during and shortly after a single WBHT treatment (11). These lesions had not recurred one year later (12) and have not recurred now, three years later. Since 1990, 31 patients with HIV and Kaposi's sarcoma have been treated by WBHT, most of them in Rome, Italy. Most of the patients had remission of Kaposi's lesions and diminished evidence of HIV for 4 months (120 days) after treatment (29).

Hyperthermia also helps to resolve many bacterial infections. The fever response in mammals evolved specifically for this reason, and beneficial effects of fever in survival of animals after gram negative blood infection has been reported (13). Hyperthermia also has a beneficial effect in resolution of many viral infections. Hornback and co-workers have studied infection of mice by Friend virus complex, a retrovirus complex similar to HIV which causes a uniformly fatal erythroleukemia in mice, with devastating effects on T-cells and natural killer cells similar to those of HIV. This disease can be partially controlled by WBHT at 40° C. (once weekly for 2 weeks). Mice receiving WBHT after injection with Friend virus lived twice as long as untreated controls, and longer than those treated with cyclosporin alone (14,15). Natural killer cell function is also increased by the WBHT therapy versus controls (14,15).

The HIV virus is somewhat heat sensitive. McDougal, et al. incubated HIV at temperatures ranging from 37° to 60° al. and found the log kill followed first order kinetics (6). In the natural liquid state, HIV was 40% inactivated after 30 minutes at 42° C., and 100% inactivated at 56° C. (17). Importantly, HIV-infected lymphocytes are very effectively killed by 42° C. temperature. Since only a small portion of lymphocytes are HIV infected, this means that the surviving cells will be free to perform their usual immunologic functions, unimpeded by HIV. Even if some HIV-infected lymphocytes do survive, they have a change in surface antigens to allow recognition by the immune system.

The beneficial effects of a single WBHT in treatment of HIV and Kaposi's sarcoma are no longer a theoretical possibility but a demonstrated reality. One study indicates that of 31 patients with HIV and Kaposi's sarcoma treated with WBHT, 70% had complete or partial regression of Kaposi's sarcoma lesions and these patients had an increase of CD4 counts for an average of 120 days. Adenopathy and oral leukoplakia resolved in all patients. The treatment was most effective when the pre-treatment CD4 count was over $50/mm^3$. In no patient was HIV activity stimulated by WBHT, as determined by many antigen markers (29).

An article by Milton B. Yatvin, PhD, indicates that "the initial effect of hyperthermia on cells is mediated via the heat-induced disorganization of membrane lipids" (28). This effect was further defined in later studies (18,19). Yatvin also described a variety of simple compounds which have fluidizing effects on lipid bilayer membranes similar to heat, and exert antiviral effects on HIV and other viral infections (including ethanol, anesthetics, AL721, adamantane, and a common food additive called butylated hydroxytoluene or BHT) (18). In later work, Yatvin suggested that the effects of heat on virally-loaded cells was enhanced by fluidizing chemical agents (27,18). These articles demonstrate that WBHT should have positive effects on HIV infection, and that these effects can be improved by addition of some simple chemicals during or before WBHT.

There are many methods for inducing WBHT including paraffin wax baths, radiant heat chambers, microwave heat chambers, water blankets, and extracorporeal blood heating.

These methods have been used mostly in treatment of patients with far-advanced metastatic cancer. Even in these frail patients, core temperature can be maintained at 42° C. for one to two hours without untoward effects on cardiovascular, renal, or liver function, though there usually is elevation of serum transaminases, creatinine phosphokinase, and lactate dehydrogenase (4). Three instances of mild neurologic damage were noted in Parks' patients in association with hypophosphatemia during treatment, but no significant problems occurred once phosphate levels were maintained (20). Larkin also reported two deaths in patients receiving WBHT at 41.5 to 42° C. for 1½ to 2 hours; however, these patients had massive tumors in the liver, and by-products of tumor necrosis contributed to the death of these patients (21). In review of prior studies Yatvin, Stowell and Steinhart found only 6 deaths in 275 hyperthermic treatments of debilitated patients with carcinoma, representing a mortality of only 2% (27).

Extracorporeal WBH is usually accomplished using a relatively simplistic circuit containing only a blood pump and a heat exchanger to heat the blood (22). The blood flow rate through the extracorporeal system has been high, at 2–3 liters per minute. During this procedure, and other WBH techniques, the patient is warmed to a core temperature of 41.5° to 42° C. for two hours or more. Sedation is required and often general anesthesia and intubation is performed (22). In the mildly sedated patient, the brain stem responds with hyperventilation, to increase heat loss. Blood alkalosis results, leading to decreases in potassium, calcium, phosphate, and magnesium (as these substances transfer into cells or bone) (23). In a generally anesthetized patient on mechanical ventilation, normal ventilation can be provided. However, the increased body metabolic rate and centralization of blood flow leads to acidosis, with increases in potassium, calcium, phosphate and magnesium (24). Frequent blood chemistries must be measured during the treatment, so that these changes in blood chemistries can be corrected by intravenous infusion of various electrolytes. Following WBH, there is often a persisting deficiency in potassium, calcium, and phosphate unless these have been aggressively replaced during the treatment. Often, there is moderate damage to liver, muscles, and kidneys during the treatment, demonstrated by changes in enzyme and toxin levels in the blood (23,25,26).

Clinically recognizable complications of hyperthermia depend to some degree upon the method of administration, whether by direct skin contact, radiant heat, or heating of the blood, and on the core temperature obtained and length of exposure. Skin burns with hyperthermia generally occur only when created by skin contact or radiant heat. Studies in cancer patients have shown a significant incidence of fatigue, peripheral neuropathy, vomiting, diarrhea, and arrhythmias. However, these occurred mostly in severely debilitated patients with Karnofsky Scores less than 50% (1,2).

In treatment of patients with HIV and Kaposi's sarcoma, hyperthermia also is relatively safe. In a study of 31 patients with HIV and Kaposi's sarcoma treated by extracorporeal WBHT with a relatively low blood flow rate of 300–400 ml/min (29), there was no significant morbidity associated with the treatment, though two patients had intravascular coagulopathy (without signs of bleeding) and several patients had pressure point skin damage. There were two patient deaths within 120 days of the procedure, one from intracerebral bleed due to a pre-existing intracerebral Berry aneurysm (a rare condition) and one from pulmonary edema and cardiac arrhythmia following overly aggressive fluid therapy (in a patient who had pre-existing pulmonary disease). The overall mortality of this study was only 7%; the mortality rate would have been zero if patients with abnormal pulmonary status had been excluded from the study, and if the patient with the very rare cerebral vascular condition had not been treated.

Among the known protocols for extracorporeal heating of blood, various difficulties persist, including elevated serum transaminases and bilirubin, instances of neurologic damage associated with serum hypophosphatemia, risk due to abnormal pH or to abnormal sodium, sodium bicarbonate or potassium levels, and possible death from massive tumor necrosis. Previously attempted treatments of human immunodeficiency virus with hyperthermia have included only relatively minor measures to maintain normal blood physiology (the sodium bicarbonate addition of Davidner et al., for example). A need therefore remains for a more reliable, simpler and more comprehensive extracorporeal hyperthermia treatment, and an apparatus for performing such treatment, in which unwanted side effects are reduced or eliminated altogether. The present invention addresses this need.

SUMMARY OF THE INVENTION

One preferred embodiment of the invention provides an apparatus for use in whole body hyperthermia treatment of a patient. The inventive device comprises a dialyzer having a blood inlet to and a blood outlet from a blood side separated from a dialysate side by at least one dialysis membrane, said dialyzer further having a dialysate inlet to and dialysate outlet from said dialysate side. The apparatus further includes a blood circuit for conveying blood from the patient to said blood inlet and from said blood outlet back into the patient, and a pump operably associated with said blood circuit for circulating blood through said blood circuit. A heat exchanger is operably associated with the blood circuit and preferably effective to heat blood circulating in the blood circuit to a temperature of at least about 40° C. A sorbent suspension is provided in the dialysate side of the dialyzer, which includes at least the components water, a particulate surface adsorptive agent, and precipitated calcium phosphate. Circulating means are also provided for circulating said sorbent suspension in said dialysate side of said dialyzer in a direction generally from said dialysate inlet to said dialysate outlet. A preferred device further includes a heater, such as an electrically-powered device which generates heat via resistance to electric current, associated with the dialysate side and effective to heat the sorbent suspension to a temperature of at least about 40° C.

Another preferred embodiment of the invention provides a composition for use as a dialysate in hemodialysis. The inventive composition comprises a sorbent suspension which includes water, a particulate surface adsorptive agent, a particulate cation exchanger, a surface active agent, and precipitated calcium phosphate.

Another preferred embodiment of the invention provides an apparatus for use in whole body hyperthermia in which relatively high rates of blood flow can be established in a hemodialysis instrument while maintaining proper sorbent mixing by the expansion and compression of compliant membranes of the instrument. The inventive apparatus comprises a dialyzer having a blood inlet to and a blood outlet from a blood side separated from a dialysate side by dialysis membranes, the dialyzer further having a dialysate inlet to and dialysate outlet from said dialysate side, the membranes being compliantly formed to expand and compress in response to alternating negative pressure and positive pressure on said dialysate side of the dialyzer so as to agitate a sorbent suspension to prevent settling. The apparatus also includes means for applying alternating negative pressure and positive pressure on the dialysate side of the dialyzer, and a blood circulation circuit. The blood circulation circuit includes a blood removal circuit for conveying blood from the patient to the blood inlet of the dialyzer, and a blood return circuit for conveying blood from the blood outlet back into the patient. The blood removal and return circuits are adapted for connection to the patient via separate accesses. One or more pumps operably associated with the blood circulation circuit are operable to circulate blood through the blood circulation circuit in a direction generally from the blood removal access to the blood return access. Bypass means fluidly connect the blood removal circuit to the blood return circuit, and allow blood circulated by the pump to bypass the dialyzer so as to reduce blood-side tensioning of the dialyzer membranes whereby effective mixing of the sorbent suspension can be maintained. A heat exchanger is operably associated with the blood circulation circuit and is effective to heat blood circulating in the blood circulation circuit.

It is an object of the invention to provide an apparatus which can effectively be used in whole body hyperthermia to control patient blood chemistries during the treatments, including effective control of calcium and phosphate levels.

Another object of the invention is to provide a sorbent suspension composition which is highly effective for use in sorbent-based hemodialysis to control patient blood calcium and phosphate levels in addition to other blood chemistries.

Another object of the invention is to provide an apparatus for use in supplying hemodialysis during whole body hyperthermia, which apparatus includes compliant membranes which promote mixing of sorbent suspensions and which are not overly tensioned by high rates of blood flow used during the treatments.

Additional embodiments, features and advantages of the present invention will be apparent from the following description.

DESCRIPTION OF THE PREFERRED EMBODIMENT

Figure 1:
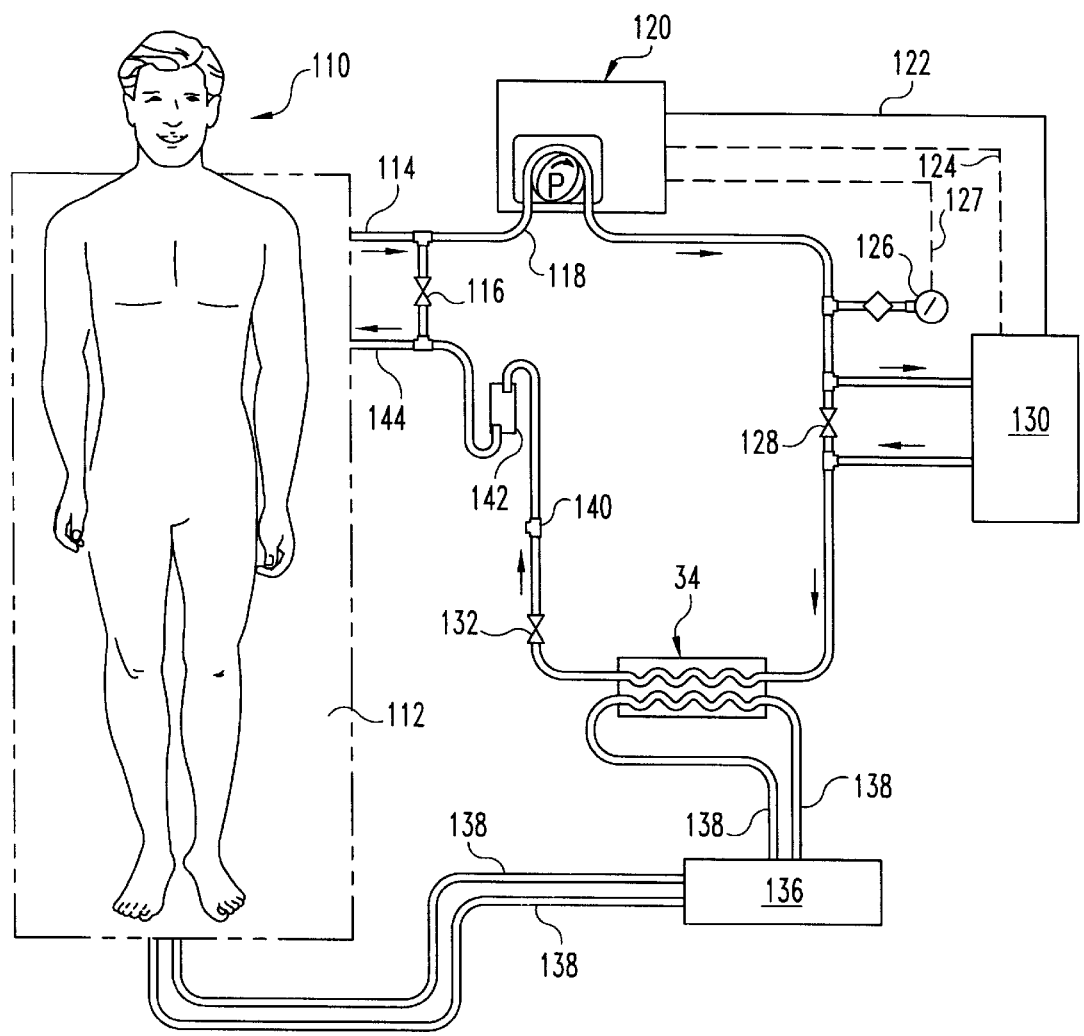
FIG. 1 is a schematic diagram illustrating a preferred apparatus for conducting whole body hyperthermia.

For the purpose of promoting an understanding of the principles of the invention, reference will now be made to certain embodiments thereof and specific language will be used to describe the same. It will be understood, however, that no limitation of the scope of the invention is thereby intended, such alterations, further modifications and applications of the principles of the invention being contemplated as would normally occur to one skilled in the art to which the invention pertains.

The present invention enables the application of sorbent-based hemodialysis to hyperthermia treatments in a highly effective fashion. This hemodialysis technology involves the use of a specialized sorbent suspension as the hemodialysing solution. The dialysis procedure during hyperthermia allows many important electrolytes to be regulated and kept at appropriate levels in the blood. In addition, many toxins, for example those incident to death of virally infected cells and/or Kaposi's sarcoma cells, are removed.

The sorbent suspensions used in the invention generally include powdered surface adsorptive agents, physiologic electrolytes and macromolecular flow inducing agents. In general, these components are present in effective amounts to achieve the desired removal of substances from the electrolyte balance in the blood of the patient while maintaining the stability and fluidity of the sorbent suspension. The powdered surface adsorptive agent is usually activated charcoal, preferably with an average particle diameter not exceeding about 100 microns. Even more preferably, the average particle diameter does not exceed 50 microns. Macromolecular flow inducing agents such as glycol derivatives help to maintain the flow properties and stability of the particle suspensions.

The sorbent suspensions generally include various electrolytes, typically including one or more electrolytes selected from sodium, chloride, bicarbonate, potassium, calcium, magnesium, or any other electrolytes to be regulated in the patient.

The sorbent suspensions also may include ion-exchange substances to bind ions, such as ammonia, which may appear in the patient's blood. Many suitable ion exchangers including polymeric ion exchangers, e.g. polystyrene sulfonate, and zeolites, are known in the art and can be used in the present invention. When included, the ion-exchanger is preferably a cation-exchange resin, which is desirably loaded with one or more cations representing electrolytes occurring in blood. For example, to date, sodium polystyrene sulfonate has been a preferred cation exchange resin. For use in conjunction with whole body hyperthermia, the cation exchangers are preferably heavily loaded with Ca, K and Mg ions at the start of hyperthermia in an amount to be substantially in equilibrium with the normal blood concentration of these cations.

The surface adsorptive agent, electrolytes, flow inducing agents and any other additives will usually comprise about 5% to 30% by weight of the sorbent suspension formulation as a whole, with the remainder being water. Typically, solid sorbents will comprise about 2% to 25% by weight of the suspension formulation, and electrolytes will comprise about 1% to 5% by weight of the suspension formulation. Within these parameters, more preferred sorbent suspension formulations comprise about 2% to 20% by weight powdered surface adsorptive agent, up to about 10% by weight ion-exchanger, and up to about 1% by weight flow or surface active agent such as a polyol and/or polyvinylpyrrolidone (PVP).

In accordance with one aspect of the invention, the sorbent suspension also includes solid or precipitated calcium phosphate, which is used to assist in the control of calcium and phosphate levels in the blood of the patient. Controlling plasma phosphate concentration is somewhat more complicated that controlling other blood components. In the body, calcium and phosphate concentration are determined by their mathematical product. When the concentration of calcium in blood plasma increases, calcium phosphate precipitates on bone and the plasma phosphate level falls. Conversely, when plasma calcium concentration decreases, calcium phosphate is solubilized and plasma phosphate levels increase. In the present invention, the calcium phosphate precipitate in the sorbent suspension effectively mimics the body's calcium phosphate system, achieving control of calcium and phosphate levels. Thus, when the blood phosphate level decreases, calcium phosphate in the sorbent suspension dissolves and phosphate is released into the blood. Conversely, if the blood phosphate level increases, phosphate can be removed from the blood by precipitation of calcium phosphate in the sorbent suspension. The calcium-loaded cation exchanger moderates calcium concentration during these phosphate concentration changes. Accordingly, the sorbent suspension can be optimized to deliver more or less phosphate to a patient during treatment by adding, respectively, less or more calcium in the calcium-phosphate precipitation step in the preparation of the sorbent suspension. Because changes in blood concentrations of calcium and phosphate are not likely to be quantitatively the same during hyperthermia, 10% calcium chloride solution can also be kept available for infusion separately into blood returning to the patient, as needed.

Preferred sorbent suspensions including precipitated calcium phosphate are carefully prepared to assure that the calcium phosphate precipitate has maximal surface area for release or adsorption of calcium phosphate; forming the precipitate on the surface of the charcoal or other surface adsorptive agent achieves this goal. A preferred process for preparing a sorbent suspension includes adding sterile water for irrigation to a vessel (e.g. a sorbent bag) which contains activated charcoal powder and flow-inducing agents. Calcium chloride and sodium chloride electrolyte solutions, and a disodium phosphate solution, are then added to the vessel. The mixture is then agitated, e.g. by shaking the sorbent bag, and the cation-exchange resin added (pre-loaded with sodium, calcium, magnesium, and potassium). The contents are agitated again, and then sodium bicarbonate powder is added, followed by further agitation. This process effectively prepares a sorbent suspension containing precipitated calcium phosphate, and which is essentially free from limestone.

In such a sorbent system, the surface adsorptive agent provides surface area on which substantial amounts of calcium phosphate can be supported, and thus in the overall sorbent suspension calcium phosphate will be present supported by the surface adsorptive agent as well as generally in the mixture.

There are many dialyzer membranes which are known for use in dialysing body fluids such as blood, and these membranes may be used with the sorbent suspension as though the sorbent suspension were a simple dialysis solution. One suitable membrane of this type is a cellulosic membrane composed of regenerated cuproammonium cellulose (Cuprophan).

Sorbent suspensions as described above are advantageously used in a dialysis instrument including a parallel plate dialyzer, by moving the sorbent suspension formulation in a counter-current mode by the direct application of alternating negative pressure and positive pressure on the dialysate side, as described in more detail below.

The sorbent suspension works as follows. When blood opposes the sorbent suspension, separated only by the dialysis membrane, diffusion causes many chemicals to pass from the blood into the sorbent suspension on the other side of the membrane. Depending upon the binding characteristics of the sorbents, some chemicals remain at low concentration in the sorbent suspensions (and are therefore efficiently removed from the blood) and others reach concentrations similar to the blood (and are therefore not removed from the blood). Inclusion of certain chemicals in the sorbent suspension composition can partially saturate sorbent binding sites, and cause return of those chemicals to the blood during treatment. Thus, the sorbent suspension may be tailored to remove very specific compounds from the blood, without removing others.

Also, when the above-described sorbent suspensions are used in conjunction with hyperthermia treatments, a blood pump is included in the extracorporeal blood circuit. Such external blood pumps provide fast blood flow to effect the desired body heating in the time allotted. In hyperthermia treatments fast blood flow is important to the success of the hyperthermia treatment and its reversal. A blood pump is thus used to propel blood through a blood circuit containing the heat exchanger.

The membranes used for sorbent-based dialysis allow passage of soluble chemicals under about 5,000 molecular weight. The first function of hemodialysis with sorbent suspensions is to correct abnormalities in cationic blood electrolytes including sodium, potassium, calcium, magnesium and hydrogen ions (blood pH). This is achieved by loading the cation exchanger in the sorbent with sufficient cation amounts to be at equilibrium with the desired (normal) blood levels. If the blood concentration of a particular cation is lower than the equilibrium level, the cation will be released from the cation exchanger. If the blood concentration is above normal, the cation will be absorbed by the cation exchanger.

In the present invention, the cation exchanger of the sorbent suspension has some buffering effect, to assist in maintaining normal blood pH. As a backup blood pH control, the pH of the sorbent suspension is preferably monitored, and thus preferred apparatuses will include means for monitoring blood pH. If the sorbent pH becomes higher or lower than normal blood pH, an alarm sounds, and the user can direct the system to infuse acidic or basic solutions until the sorbent pH is the same as normal blood pH.

An exemplary sorbent suspension contains: 140 grams powdered activated charcoal; 22.1 grams $NaHPO_4 * 7H_2O$ and 3.0 grams $CaCl * 2H_2O$ (added together to the charcoal suspension); 200 grams Amberlite IRP-69 cation exchange resin loaded with blood equilibrium levels of Na, Ca, Mg and K ions; 13.0 grams NaCl; 15.1 grams $NaHCO_3$; and 1.5 grams of each a glycol derivative and PVP to enhance stability and flow properties of the sorbent suspension. This is an example only, and is not intended to be limiting.

During hyperthermia, there may be other toxins which evolve, due to diminished kidney or liver function. The surface adsorptive agent (e.g. charcoal) and cation exchangers in the sorbent suspension will remove many of these toxins, including: creatinine; aromatic amino acids; gamma-amino butyric acid; phenols; mercaptans; ammonium ion; nitric oxides; and various vasodilating hormones. Naturally, the sorbent suspension is not intended to remove proteins, intercellular messengers or cells, although to the degree that albumin-bound toxins can dissociate from albumin, these can also transfer across the membranes and be bound by the sorbents in the suspension.

Heating equipment which heats a blanket over and underneath the patient, to heat the dialysate, and to directly heat the blood through a heat exchanger, is also provided in accordance with the invention. Heating/cooling blankets/mattresses and their associated equipment (an entire system of these devices is available, for instance, from Cincinnati Sub-Zero Products, Inc.) may be used without modification or with modification to permit a higher upper temperature limit.

Most preferably, the sorbent suspension is maintained at moderate temperatures so that the blood tubing, dialyzer and sorbent suspension containers contact blood only at modestly elevated temperatures. Temperatures of 42° C. are suitable for these purposes, although higher temperatures, for example up to 48° C. or more, may also be used. The heat exchanger, final microfilter and the tubing returning blood to the patient will contact blood at temperatures of about 47–48° C. in preferred processes. These same components are used in open heart surgery to warm patients and safety of contact with blood at these temperatures has been thoroughly documented.

FIG. 1 illustrates a preferred apparatus for achieving sorbent-based hemodialysis according to the present invention. The patient 110 is positioned on or between hyperthermia sources 112, which may be a heated mattress, a heated mattress with heated-air-emitting blankets, or a similar heat-imparting patient chamber. A blood outflow catheter 114 connects the patient to extracorporeal blood circuit tubing 118. The tubing 118 transports blood from blood outflow catheter 114 to a pump/heater control 120, through a pressure gauge 126 and to tubing which leads to and past a sorbent-based hemodialyzer 130. The pump/heater control 120 and the sorbent-based hemodialyzer 130 are connected by a heater power line 122 and a heater temperature feedback control line 124, whereas the pump/heater control 120 and the pressure gauge 126 are connected by a pressure gauge feedback line 127. A hemodialyzer bypass control valve 128 is provided on the tubing passing the inlet and outlet of the hemodialyzer 130 to normally allow some of the circulated blood to bypass the hemodialyzer when open, or to pass all blood through the dialyzer when closed. After the blood has passed through or past the hemodialyzer, it enters a heat exchanger 134 where it is heated, by heated water generated from a hyperthermia unit 136. The hyperthermia unit 136 also provides heat to the hyperthermia sources 112 via hyperthermia unit heater lines 138. After the blood is heated in heat exchanger 134, it passes through temperature gauge 132 and flows back to the patient 110 through a blood sample port 140. Air bubbles are removed from the blood in a drip chamber and micro bubble filter 142 located between sample port 140 and a blood return catheter 144. The blood outflow catheter 114 and blood return catheter 144 may be separate arterial and venous catheters or a single, double-lumen structure which is well known in the art. Regardless of how catheters 114 and 144 are configured, they are connected by a bypass control valve 116 to provide the option of immediate return of blood to the patient, should need arise, without the blood's traveling through the entire extracorporeal circuit. The pump/heater control 120 imparts some heat to the blood through heating the sorbent suspension, but preferably does not raise the sorbent suspension temperature above about 42° C. In this way, heat loss from the body is avoided when the body core temperature increases to 42° C.

Blood flow rates of 300–800 ml/minute will be typical, with flow rates of about 300–600 ml/minute being preferred. Centrifugal pumps or "roller pumps" capable of achieving these blood flows are known in the art, and typically are the same pumps used for heart perfusion during so-called "open heart" surgery. Referring once again to FIG. 1, such a roller pump appears as the pump/heater control 120.

Figure 2:
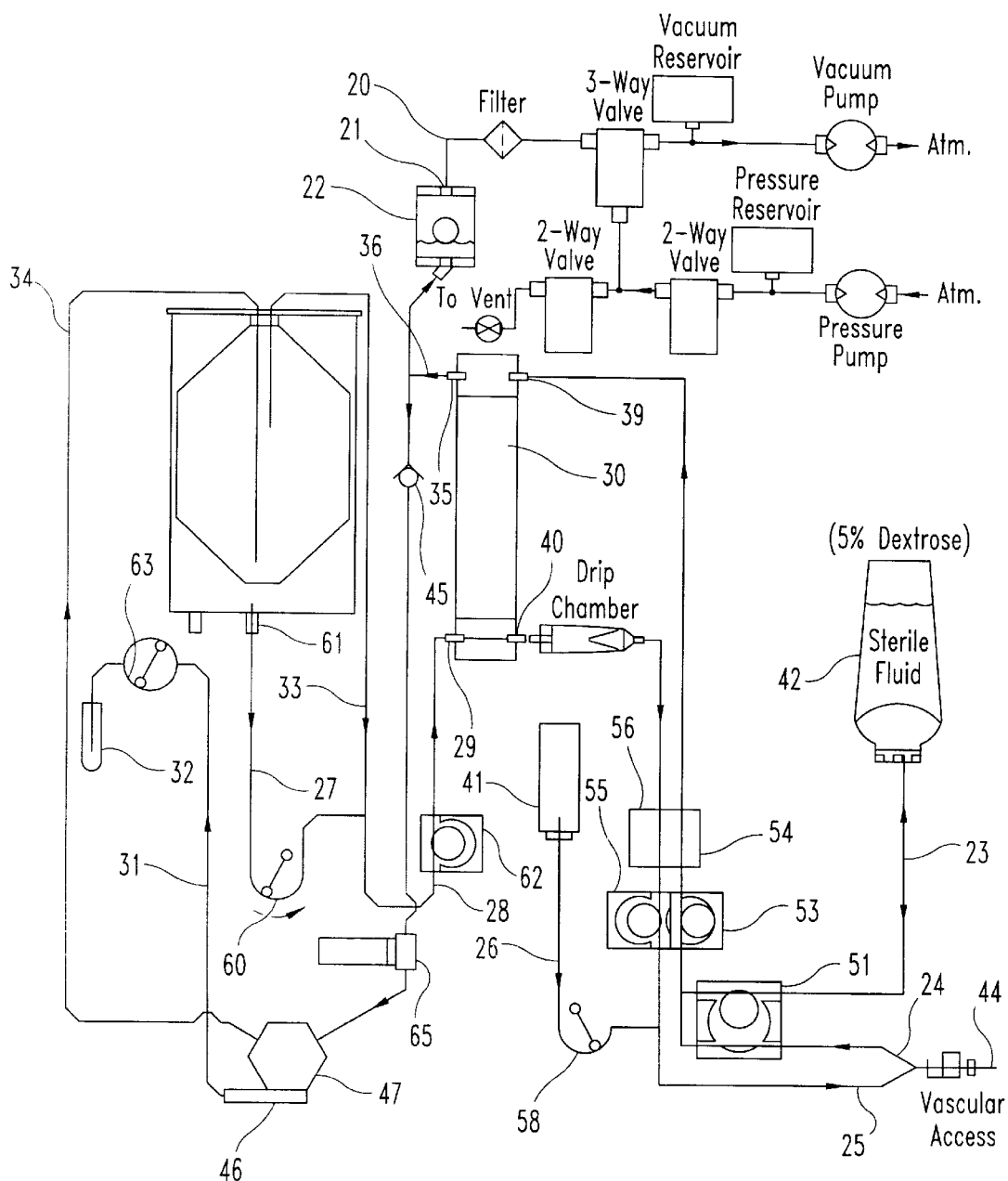
FIG. 2 is a schematic diagram of the hydraulics of a preferred hemodialysis instrument used in the conduct of whole body hyperthermia.
Figure 3:
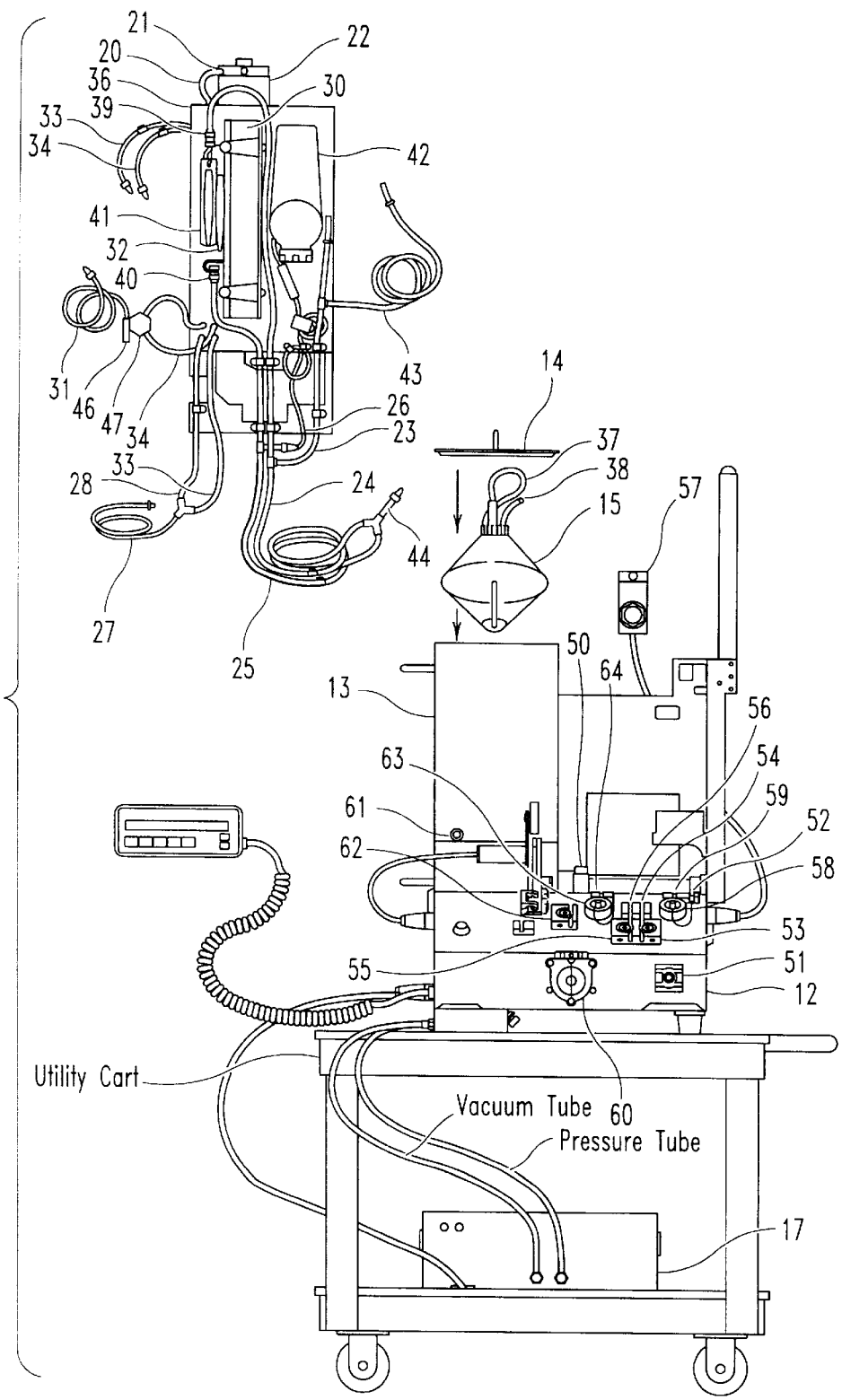
FIG. 3 provides a perspective view of components of a preferred hemodialysis instrument used in the present invention.

Referring now to FIGS. 2 and 3, shown are a schematic diagram illustrating the hydraulics of the preferred hemodialysis unit used in the invention, and a perspective view of the preferred dialysis system used in the invention. The dialysis system is similar to that disclosed in U.S. Pat. No. 5,277,820, with several important modifications. Thus, the dialysis system 11 includes a machine base 12, reservoir tank 13 with cover 14, a sorbent bag 15 containing sorbent suspension materials, disposable pack 16 (including the plate dialyzer), and power supply 17 (providing vacuum, pressure, and DC power to the machine base). Vacuum/pressure line 20 from top port 21 of accumulator 22 is connected to sources of vacuum and pressure in power supply 17. Prime tube 23 is seated into the upper side of prime/rinse clamp 51 and through prime fluid sensor 52. The blood inflow tube 24 is seated into the lower side of prime rinse clamp 51, blood inflow clamp 53 and the blood inflow sensor 54. The blood outflow tube 25 is seated into blood outflow clamp 55 and blood outflow sensor 56, and fluid level sensor 57 is placed onto accumulator reservoir 22. Reinfusate tube 26 is loaded into reinfusate pump 58 and reinfusate fluid sensor 59. Dialysate tube 27 (prior to the "Y" split) is loaded into dialysate pump 60 and its end connected to water port 61. Branch of dialysate tube 28 (after the "Y" split) which connects to the dialysate inlet 29 of dialyzer 30 is seated into dialysate-in clamp 62. Filtrate line 31 is loaded into filtrate pump 63 and into filtrate fluid sensor 64. Filtrate line 31 is also connected to filtrate disposal bag 32 which is vented. Three liters of sterile water are added to reservoir tank 13. Sorbent bag 15 is suspended from reservoir cover 14. Tubes 33 (leading to dialysate inlet 29) and 34 (leading to the exit port of accumulator 23 and also connected to dialysate outlet 35 via line 36) are connected to lines 37 and 38 provided on and leading into sorbent bag 15.

The following steps are conducted under sterile conditions. Blood inflow line 24 and blood outflow line 25 are connected to blood inlet 39 and blood outlet 40 of dialyzer 30, respectively. Reinfusate solution (e.g. CaCl$_2$ solution and appropriate amounts of KCl and/or NaCl solution) is injected into reinfusate bag 41. Reinfusate line 26 is connected to reinfusate bag 41 and a drip chamber in the line is partially filled. Prime tube 23 is connected to prime bottle 42 containing priming fluid, e.g. 5% dextrose. If desired, replacement fluid can be provided via fluid replacement line 43.

The blood inflow 24 and blood outflow 25 tubes pass from separate access lines in the patient, with a bypass provided, as illustrated in FIG. 1, through clamps 53 and 55 and optical monitors 54 and 56 to connect to the top 39 and bottom 40 openings of the blood side of the dialyzer 30. Cylindrical accumulator 22 attaches to the dialysate space at the top opening 35 of the dialysate side of dialyzer 30, and alternating strong vacuum (i.e. negative pressure) and modest positive pressure in accumulator 22 (provided by line 20 through port 21 above the fluid level) alternately draws dialysate into and expels dialysate from accumulator 22, which expands and compresses the membranes of dialyzer 30, while the automatically controlled blood inflow and outflow clamps 53 and 55 assure that blood passes unidirectionally through the dialyzer 30.

In the preferred dialysis system 11 utilized in the specific Examples, the dialyzer was a 1.6 m$^2$ COBE parallel screen-plate dialyzer having dialysis membranes composed of regenerated cuproammonium cellulose (Cuprophan) and having a functional molecular weight cut-off of about 3000 daltons, i.e. only molecules of about 3000 daltons or less will pass through the membrane.

As discussed above, the preferred system used in the invention contains a sorbent suspension in the dialysate side. Flow of the suspension is generally counter-current, and is both bidirectional between the accumulator 22 and dialyzer 30, and circular between the dialyzer 30 and sorbent reservoir 15.

In summary, during the first part of blood inflow, clamp 62 on the dialysate inflow line 33 opens, allowing sorbent suspension to flow from the sorbent reservoir 15 through the entire dialyzer 30, filling the accumulator 22 to the level of sensor 57. Clamp 62 then closes and remains closed during the remainder of inflow and all of outflow, when pressure in the accumulator 22 returns some suspension to the dialyzer 30 and passes some through one-way valve 45 to return to the reservoir 15 via dialysate return line 34. This, along with the expansion and contraction of the dialyzer membranes, keeps the sorbent suspension well mixed at the dialyzer membrane surface.

In the preferred system, the priming fluid for the blood side of the dialysis system is 5% dextrose from container 42 attached to blood inflow tube 24 via tube 23. During priming, priming/rinse clamp automatically opens prime tube 23 while closing blood inflow tube 24. Priming fluid is thus pulled into the system rather than blood.

A flow-through pH monitor 65 is situated in return line 34 to monitor the pH of the sorbent suspension which in turn gives indication of the pH of the patient's blood. The pH control is preferably established such that if the pH of the suspension exceeds 7.5 or is less than 7.2, an alarm will sound (the proper sorbent and blood pH is, of course 7.4). For pH adjustments, a bag of 2 N sodium hydroxide solution can be provided and infused at a slow rate into the sorbent suspension if desired through a roller pump, to offset any trend towards acidosis during priming operations or during the treatment. Control of the rate can be established through inputs on the pump heater control 120 (see FIG. 1). A bag of 2 N hydrochloric acid is also preferably provided so that it could be infused to correct alkalosis of the sorbent suspension. In work to date, except for the addition of a small amount of hydrochloric acid during priming, no further control of sorbent or blood pH has been needed.

As shown in FIG. 1, the blood side of the dialysis apparatus is configured differently than that disclosed in the preferred embodiment in U.S. Pat. No. 5,277,820. The addition of a roller pump in the extracorporeal blood circuit as described above provides high blood flow rates for hyperthermia. Such high blood flow rates can cause increased tensioning of the dialyzer membranes on the blood side. As a result, movement of the membranes is restricted, thus reducing sorbent mixing otherwise provided by the expansion and compression of the compliant membranes. The use of a bypass 128, as described above, has been found to preserve proper membrane motion and sorbent mixing even under high blood flow rates. Prevention of localized concentrations or dilutions of components in the sorbent suspension is thus achieved, improving the efficacy of treatment.

In addition, for use of the illustrated hemodialysis unit in hyperthermia treatments, a rod heater is placed in a chamber through which the sorbent flows on the way from the sorbent reservoir to the dialyzer. The rod heater is highly effective in transferring heat to the sorbent suspension. The default temperature setting of this heater is preferably 42° C. This can be changed by the user to any lower temperature (above 20° C.) but in the preferred embodiment cannot be increased above 42° C. The heater begins to increase the sorbent temperature during a priming operation, which reaches 42° C. by the end of the priming operation. During the dialysis/WBHT treatment, the sorbent temperature remains at 42° C., unless the heater is turned off through the control module. Control provisions are also provided such that the sorbent heater is automatically turned off during pauses in the operation of the hemodialysis unit. When the cooling phase of the patient is begun, the sorbent heater is manually turned off at the same time the air blanket is removed and the water to the water blanket and blood heat exchanger turned to cool. The sorbent suspension is cooled passively by the blood.

Prior to treatment, patients are screened for underlying heart disease; underlying lung disease (including pulmonary Kaposi's Sarcoma if one or more lesions is greater than a certain size); pregnancy; a Karnofsky score of less than 60%; a non-correctable hematocrit of less than 30 ml.; hemoglobin less than 10%; active opportunistic infection; bleeding disorders; or Diabetes Mellitus. Any of the foregoing warrants careful consideration of the risks versus the benefits of hyperthermia treatment, since an important consideration in the practice of the present technique is whether the patient can tolerate it. The prehyperthermia evaluation requires a routine history and physical examination, routine laboratory studies, chest x-rays, urinalysis, electrocardiogram and pulmonary function studies. Special studies include P-24 antigen level assay; reverse transcriptase assay; human immunodeficiency virus cultures; lymphocyte quantitative analysis and thyroid profile.

The present protocol is preferably conducted using conscious sedation and/or analgesics. The use of sedative amounts—as distinct from anesthetic amounts—of thiopental sodium is preferred. An exemplary analgesic is commercially available as Sublimaze (fentanyl citrate, or N-(1-phenethyl-4-piperidyl)propionanilide citrate), a synthetic narcotic analgesic. An exemplary conscious sedation-inducing drug is Propofol, which is a sedative (or hypnotic agent) widely used in outpatient applications. The chemical formula for Propofol is 2,6-diisopropylphenol; the commercial name is Diprivan injection. These drugs are exemplary only, and the invention is not to be considered as limited to these illustrative medications. (However, Versed (midazolam hydrochloride, or 8-chloro-6-(2-fluorophenyl)-1-methyl-4H-imidazol[1,5-a][1,4]benzodiazepine hydrochloride), a short-acting benzodiazepine central nervous system depressant, should not be used, and other benzodiazepine derivatives are likewise contraindicated. Midazolam hydrochloride and benzodiazepine derivatives in general are biologically incompatible with hyperthermia: while Versed demonstrates typical pharmacologic activity (including reversibility) during the present procedure, the combination of the hyperthermia with the body biochemistry incident to hyperthermia causes disastrous central nervous system trauma (and possible death) six hours after the procedure is complete.) With the patient sedated, but not unresponsive, central nervous system activity can readily be monitored during hyperthermia treatment. When the sorbent-based hemodialysis is used, the sorbents clear approximately 50% of the sedative from the bloodstream. Therefore, administration of approximately twice the dosage of sedative will give the same sedative effect as when no dialysis is used.

Modification of the sorbent suspension may also be used to control other blood chemistries. For example, the sorbent suspension may be loaded with a sedative such as thiopental sodium to be in equilibrium with a level causing sedation. The patient blood level would then quickly rise to this level during hyperthermia treatments of the invention. Further sedation could be achieved by administering an injection of thiopental sodium to the blood; the pre-loaded sorbent suspension would then not remove significant amounts of the drug during treatment. Other agents for augmenting the hyperthermia treatment could also be loaded into the sorbent suspension and delivered during treatment, to maintain a reasonably constant blood concentration of the agents.

Because of the patient's natural depletion of carbohydrate and fat stores, these substances should be administered during and/or after treatment to assure that these precursors are adequately available to marginally competent metabolic pathways. Hemodialysis maintains levels of phosphate and calcium during treatment—which levels would otherwise fall as a result of the hyperthermia—especially when acid/bicarbonated water is used as the dialyzing solution. Maintenance of arterial oxygen tensions as high as possible during hyperthermia by use of 100% oxygen for ventilation should satisfy the need to maintain greater than normal blood and tissue oxygen tensions necessitated by hyperthermia-increased oxygen consumption.

The invention may be further illustrated by means of the following examples.

EXAMPLE 1

Animal Studies

A. Normal Calves

Tests were performed to determine the safety of WBHT. These animal experiments were performed with the apparatus depicted in FIG. 1, except that no heating blanket was employed. The sorbent temperature at 44° C. during the treatments. Nine normal holstein calves, average weight 70 kilograms, were sedated with Rompun to a level which caused a slow but regular respiratory rate. If respirations became slow and irregular, the animals were intubated and placed on mechanical ventilation (this was necessary in 3 animals). By dissection, 16 French cannulas were inserted in the carotid artery and vein, an intra-arterial temperature probe was placed through the carotid artery, and another temperature probe was placed in the esophagus. The treatment raised the core temperature to 42° C. for 35–55 minutes; the animals were then cooled to normal blood temperature. Blood chemical values and cellular counts were measured frequently during the treatment. After treatment, the catheters were removed, the incisions closed, and the animals allowed to awaken. The animals were observed for the next 30 days, and had blood tests drawn each week. No prophylactic antibiotics were administered to the animals.

All of the animals achieved 42° C. core temperature, and all survived the hyperthermic procedure. None of these animals developed evidence of bleeding tendency or DIC. Slight increases in SGOT and SGPT occurred in all animals, and an increase in alkaline phosphatase occurred in six animals. Serum potassium increased slightly in a few animals, due to the fact that potassium was added to the calcium chloride in the replacement fluid. No calf died within 24 hours of the procedure. One died 14 days after the procedure, due to pneumonia (confirmed by autopsy). This complication might have been avoided if prophylactic antibiotics were administered. Another calf expired 28 hours after the treatment from pulmonary edema (confirmed by autopsy, with no other pathological changes noted in any organ). Each of these calves had been intubated and placed on a respirator during WBHT. Evaluation of the treatment of this calf led to the conclusion that if fluid replacement had been performed according to a protocol to maintain pulmonary wedge pressure or central venous pressure at normal levels, acidosis and hypotension would have been prevented, as well as the cardiac damage which eventually led to pulmonary edema.

These animal studies, performed with minimal cardiovascular monitoring, indicate that the treatment is generally safe, with all animals surviving the procedure and two late complications. Administering fluids according to the need, as indicated by Swan-Ganz catheter, careful antisepsis techniques during catheter placement, and administration of prophylactic antibiotics would have diminished the animal mortality of this study to zero.

B. Pig

An animal study was designed to closely monitor the chemical changes which occur during WBHT treatment. In this study a normal pig of 20 kg weight was treated in accordance with the general procedure in Example 1(A), with sorbent temperatures of 48° C., to provide a more strenuous test for the equipment, blood and subjects. After sedation with Rompun, the pig was intubated and allowed to breathe naturally. Temperature monitors were placed in the esophagus, bladder, and rectum. By surgical cutdown, 8 French catheters were placed in femoral artery and femoral vein, and a Swan Ganz catheter placed in the pulmonary artery. The apparatus was attached to the femoral artery and vein catheters, blood flow was set at 450 ml/min, and within 30 minutes the core temperature of the animal reached 42° C.

Blood sodium and potassium concentrations remained normal during the procedure. Blood calcium and magnesium concentrations remained normal during the procedure, while an abnormally elevated phosphorus level fell towards normal during the procedure. The results demonstrate that when the apparatus of the invention is used in WBHT, blood chemistries either remain normal or become more normal.

C. Simian Immunodeficiency Virus (SIV)-Infected Rhesus Monkey

SIV is a retrovirus highly similar to HIV in its physical characteristics and in its effects on the body. To investigate the effect of WBHT on primates with this infection, an 8 kilogram Rhesus monkey infected with SIV was treated according to the general procedure of Example 1(A). The sorbent temperature was 48° C.

The animal was anesthetized and intubated, and 8 French catheters were placed in the femoral artery and vein. A Swan-Ganz catheter was placed, and fluid management was according to the protocol for human treatments. The apparatus was attached to the femoral catheters, and blood treatment rate set at 200 ml/min (a high rate, considering the small size of the animal). Within one hour the core temperature of the monkey reached 42° C., and this core temperature was maintained for one hour. Blood sodium and potassium concentrations remained normal during and after the treatment. Calcium and magnesium remained normal during and after the treatment, though phosphorous declined during the treatment (leveling out probably due to phosphate replacement from the sorbent). Blood pH was maintained at a normal value in spite of slightly falling $pCO_2$ and $HCO_3$ levels. Urine output remained relatively constant during the treatment, and increased after the treatment. There was an immediate drop in hematocrit at the start of the treatment (due to dilution of the blood volume by the extracorporeal circuit volume), but the hematocrit remained stable during the rest of the treatment.

Blood drawn before and after the treatment indicated no change in liver enzymes, creatinine, electrolytes or other laboratory values. There was a drop in albumin concentration and platelet count, partly accounted for by dilution of blood by the volume of the extracorporeal circuit, and by the huge surface area of the circuit relative to the animal's size.

The monkey survived the treatment and was returned to his cage shortly after the procedure, in good health. On the first day after treatment, the animal appeared in good health. On the second day after treatment, the animal was found in the cage without pulse or respiration, still warm. An autopsy was performed, which showed no macroscopic or microscopic pathology of any organ system, and no signs of significant internal bleeding (in spite of a drop in blood platelet concentration during the treatment). Dr. James Blanchard, director of the Tulane Primate Center, reviewed all data related to the case and stated in a letter that the death of the animal "was not related any side-effect of the treatment," even though it was not clear just what caused the death. Tissue samples were submitted for determination of viral load by the limiting dilution PCR test. Compared to titers determined on tissue just before the treatment, the viral load had diminished from a titer of 1:64 to 1:32. Though this change is not statistically significant, it is impressive, given the short time between treatment and measurement of the titer.

EXAMPLE 2

Treatment of HIV-Infected Patients with KS

Two patients with HIV infection and Kaposi's Sarcoma were treated as follows. The treatments were performed in Santo Domingo, under approval of the Director of the Ministry of Health. Screening techniques were as follows. A pre-operative evaluation included: biopsy of any existing Kaposi's Sarcoma lesion; complete blood cell count; biochemical profile; electrolytes; antigen P24; reverse transcriptase assay; western blot; human immunodeficiency virus antibody; immunologlobin assay; lymphocyte fractions (including $CD_4$); coagulation studies; spirometry; and echocardiogram. Patients were selected for treatment in this study if they were between the ages of 18 and 40, tested positive for the human immunodeficiency virus, had Kaposi's sarcoma as a result of HIV, and had normal or at least 80% normal pulmonary, cardiac, renal and hepatic functions. (Patients were excluded from this study if they exhibited severe immunodepression, extensive Kaposi's lesions in vital organs, were at cardiac risk or had radiation of the mediastinum or vital organs.)

The first patient was a 38 year old male having had known HIV infection for about four years. In 1989 he developed numerous nodular, red-violet colored lesions on both feet, the abdomen and the back. Biopsies in 1989 and 1993 confirmed the lesions to be Kaposi's Sarcoma. The leg lesions, which bothered the patient the most, had previously been irradiated many times, but had only partially responded. The largest lesion, on the dorsum of the right foot was quite painful and tender, and developed during 1993. Other symptoms of HIV included diarrhea and weight loss, though the patient's physical examination was normal and he appeared reasonably able to complete daily activities. He had not taken any medications for HIV infection, but had taken antibiotics intermittently.

Treatment was performed with the apparatus illustrated in FIG. 1, with a sorbent suspension temperature of 48° C. Access was established using an ultrasound-guided needle under local anesthesia, and the following were positioned: a 7 French Swan-Ganz catheter through a femoral vein (and advanced into the pulmonary artery); an 18 gauge catheter in a femoral artery for arterial pressure monitoring; a 10 French catheter in a femoral artery; and a 10 French catheter in a femoral vein. Through a peripheral vein, 100 mg thiopental sodium was administered, and the procedure begun. The patient was given 4000 units of heparin at the start of the procedure, and 2 mg of dexamethasone, as planned. By blood clotting tests, the patient required one more injection of 2000 units of heparin during the treatment. Fluid replacement in the patient was effected according to the skill of the art, to keep the wedge pressure constant at its starting value; 3 liters of normal saline were administered total. A total of 700 mg thiopental sodium was administered during the procedure. Calcium chloride infusion to blood was made at the rate of 5 ml/hour.

Blood flow in the extracorporeal circuit was begun at a rate of 500 ml/minute, and was increased slowly to 600 ml/minute. The sorbent suspension contained 140 grams powdered activated charcoal; 22.1 grams $Na_2HPO_4*7H_2O$; 12.2 grams $CaCl_2*2H_2O$; 100 grams Amberlite IRP-69 cation exchange resin loaded with blood equilibrium levels of Na, Ca, mg and K ions; 8.8 grams NaCl; 15.1 grams $NaHCO_3$; and 3 grams of a glycol derivative to enhance stability and flow properties of the sorbent suspension, and its temperature remained stable at 48° C. during the treatment (as did the water temperature), and the temperature of blood leaving the heat exchanger reached nearly 47° C. When esophageal and rectal (core) temperature reached 42° C., the water temperature was decreased from 48° C., and the exiting blood temperature dropped to 45° C. (while core temperature remained constant). It was pre-planned that the patient would be heated to a core temperature of 42° C. for only a half hour's duration, so the cool-down period was begun at 90 minutes of treatment. The procedure ended 140 minutes after it had begun, and all catheters were removed and rinsed (except the Foley catheter—left in place for post-procedure urine collection). Encyclopedic records of blood levels and organ functions were kept throughout the procedure.

The patient's antigen status by PCR changed 4 weeks post treatment, from positive to negative, indicating a decrease in viral load in body and blood. The morning after the procedure the patient stated he had no pain and was "filled with vigor" and felt great. Over the course of the first post-procedural week, the largest lesion, on the right foot, decreased 50% in size and by two weeks post treatment the lesion had only 25% of its original size and was much less tender and painful. It remained so at 8 weeks post procedure.

The second patient was a 28 year old patient who had become HIV positive about three years earlier. Beginning in December of 1992, he developed black to purplish lesions on his right arm, then on his left arm, then over his entire body including forearms, legs, chest, nose and face. Biopsy proved the lesions to be Kaposi's Sarcoma. Therapy in 1993 included radiation which only made the lesions look slightly less dark and did not change the size at all. Intra-lesion injections of cytotoxins made the lesions more solid. The patient had taken AZT but had quit, not perceiving any benefit. Though the patient exercised frequently and ate well, he had lost 25 pounds in the preceding year, dropping from 145 to 120 pounds.

Treatment was performed, again with a 48° C. sorbent suspension temperature, according to the same protocol described for the first patient except with minor adjustments in dosages. Patient wellbeing improved according to the patient's comments post procedure, and the Kaposi's Sarcoma lesions faded. The patient gained 5 pounds and maintained this weight.

While the invention has been described in detail in the foregoing passages, the same is to be considered illustrative and not restrictive in character, it being understood that only the preferred embodiments have been shown and described and that all changes and modifications that come within the spirit of the invention are desired to be protected.

REFERENCES

The following references, and all other publications cited herein, are hereby incorporated by reference as if each had been individually incorporated by reference and fully set forth.

1. Bull JMD. An update on the anticancer effects of a combination of chemotherapy and hyperthermia. Cancer Res 1984; 44:487.
2. Robins H I, Dennis W H. Role of whole body hyperthermia in the treatment of neoplastic disease: its current status and future prospects. Cancer Res 1984; 44:487.
3. Hornback N B. Historical aspects of hyperthermia in cancer therapy. Radiologic Clinics of North America 1989; 27:481–488.
4. Cavaliere R, Ciocatto E C, Giovanella B C, et al. Selective heat sensitivity of cancer cells: Biochemical and clinical studies. Cancer 1967; 20:1351.
5. Mondovi B, Strom R, Rotilio G, et al. The biochemical mechanisms of selective heat sensitivity of cancer cells. I: Studies on cellular respiration. Eur J Cancer 1969; 5:129.
6. Reinhold H S, van den Berg A P. Effects of hyperthermia on blood flow and metabolism. In: Field S B, Hand J W, ed. An introduction to the practical aspects of clinical hyperthermia. London; Taylor & Francis 1990; 77–107.
7. Kosa S, Maeta M. Extracorporeally induced total-body hyperthermia for disseminated cancer. Consensus on Hyperthermia for the 1990s, Clinical Practice in Cancer Treatment; 177–188.
8. Beral V et al. Kaposi's sarcoma among persons with AIDS: a sexually transmitted infection? Lancet 1990; 335:123–8.
9. Special data run by CDC from a series of Year-End Editions. U.S. Department of Health and Human Services, Public Health Service, Centers for Disease Control and Prevention, National Center for Infectious Diseases, Division of HIV/AIDS, Atlanta, Ga. Received March 1993.
10. DeMoss J L, Frazier T G, Crowley J C. Hyperthermia in the treatment of cancer. J Extra Corp Ther 1985; 17:37–43.
11. Logan W D, Alonso K. Case report: total body hyperthermia in the treatment of Kaposi's sarcoma in and HIV positive patient. Med Oncol and Tumor Pharmacother 1991; 8:45–47.
12. O'Malley S. Hyperthermia: perfusion's answer to AIDS? Perfusion Life, January 1991; 6–13.
13. Koga S, Maeta M. Extracorporeally induced total-body hyperthermia for disseminated cancer. In: Bicher H I, McLaren J R, Pigliucci G M, ed. Consensus on hyperthermia for the 1990s, Clinical practice in cancer treatment. New York; Plenum Press 1990; 177–188.
14. Shen R-N, Hornback N B, Shidnia H, Lu L, Broxmeyer H E, Brahmi Z. Effect of whole-body hyperthermia and cyclophosphamide on natural killer cell activity in murine erythroleukemia. Cancer Research 1988; 48:4561–4563.
15. Shen R-N, Lu L, Broxmeyer H E. New therapeutic strategies in the treatment of murine diseases induced by virus and solid tumors: biology and implications for the potential treatment of human leukemia, AIDS, and solid tumors. Critical Reviews in Oncology/Hematology 1990; 10:253–265.
16. McDougal J S, Martin L S, Curt S P, et al. Thermal inactivation of the acquired immunodeficiency syndrome virus human T. lymphotropic virus III/lymphoadenopaty associated virus, with special reference to antihemophilic factor. J Clin Invest 1985; 76:875.
17. Spire B, Sinoussi B F, Dormont D, Montaignet L, et al. Inactivation of lymph adenopathy-associated virus by heat gamma rays, and ultraviolet light. Lancet 1985; 1:188.
18. Barklis E, Yatvin M. The life cycle of retroviruses: the influence of hyperthermia and membrane organization. Membrane Interactions of HIV 1992, 215–236.
19. Yatvin M B, Cramp W A. Role of cellular membranes in hperthermia: some observations and theories reviewed. Int J Hyperthermia 1993; 9:165–185.
20. Parks L C, Minaberry D P, Smith D P, Neely W A. Treatment of far advanced bronchogenic carcinoma by extracorporeally induced systemic hyperthermia. Thorac Cardiovasc Surg 1979; 78:881.
21. Larkin J M, Edwards W S, Smith D E, Clark P J. Systemic thermotherapy: description of a method and physiologic tolerance in clinical subjects. Cancer 1977; 40:3155–3159.
22. Parks L C, Smith G V. Systemic hyperthermia by extracorporeal induction: Techniques and results. In: Storm F, ed. Hyperthermia in Cancer Therapy, Boston, G K Hall Medical Publishers, 1983;407–446.
23. Bull J M, Lees D, Schuette W, Whang-Peng J, et al. Whole body hyperthermia: a phase-I trial of a potential adjuvant to chemotherapy. Ann Intern Med 1979; 90:317–323.
24. Parks L C, Minaberry D, Smith D P, et al. Treatment of far-advanced bronchogenic carcinoma by extracorporeally induced systemic hyperthermia. J Thorac Cardiovasc Surg 1979; 78:883–897.
25. Bull J M, Lees D E, Schuette W H, Smith R, Glatstein E, DeVita V T. Immunological and physiological responses to whole-body hyperthermia. Presented at the Third International Symposium: Cancer Therapy by Hyperthermia, Drugs, and Radiation held at Colorado State University, Ft. Collins, Colo., Jun. 22–26, 1980.
26. Robins H I, Hugander A, Cohen J D. Whole body hyperthermia in the treatment of neoplastic disease. Radiol Clin N Amer 1989; 27:603–610.
27. Yatvin M B, Stowell M H B, Steinhart C R. Shedding Light on the Use of Heat to Treat HIV Infections. Oncology 1993; 50:380–389.
28. Yatvin M B. An Approach to AIDS Therapy Using Hyperthermia and Membrane Modification. Medical Hypotheses 1988; 27:163–165.
29. Alonso K, Pontiggia P, Sabato A, Calvi G, Curto F C, de Bartolomei E, Nardi C, Cereda P. Systemic Hyperthermia in the Treatment of HIV Related Disseminated Malignancy, Presented at the 10th Annual Meeting, American Soc. Clin. Hyperthermic oncology, October 1993, Memphis, Tenn.

What is claimed is:

1. An apparatus for use in whole body hyperthermia treatment of a patient, comprising:

a dialyzer having a blood inlet to and a blood outlet from a blood side separated from a dialysate side by at least one dialysis membrane, said dialyzer further having a dialysate inlet to and dialysate outlet from said dialysate side;

a blood circuit for conveying blood from the patient to said blood inlet and from said blood outlet back into the patient;

a pump operably associated with said blood circuit for circulating blood through said blood circuit;

a heat exchanger operably associated with said blood circuit and effective to heat blood circulating in said blood circuit to a temperature of at least about 40° C.;

a sorbent suspension in said dialysate side of said dialyzer, said sorbent suspension comprising water, a particulate surface adsorptive agent, and precipitated calcium phosphate; and circulating means for circulating said sorbent suspension in said dialysate side of said dialyzer in a direction generally from said dialysate inlet to said dialysate outlet.

2. The apparatus of claim 1 wherein the surface adsorptive agent is charcoal.

3. The apparatus of claim 1 wherein the sorbent suspension further comprises a solid particulate ion exchanger.

4. The apparatus of claim 2 wherein the ion exchanger is a zeolite or polymer resin.

5. The apparatus of claim 4 wherein the ion exchanger is a polymer resin and wherein said surface adsorptive agent is charcoal.

6. An apparatus for use in whole body hyperthermia, comprising:

a dialyzer having a blood inlet to and a blood outlet from a blood side separated from a dialysate side by dialysis membranes, said dialyzer further having a dialysate inlet to and dialysate outlet from said dialysate side, said membranes being compliantly formed to expand and compress in response to alternating negative pressure and positive pressure on said dialysate side of said dialyzer so as to agitate a sorbent suspension in said dialysate side;

means for applying alternating negative pressure and positive pressure on said dialysate side of said dialyzer;

a blood circulation circuit including a blood removal circuit for conveying blood from the patient to said blood inlet, said blood removal circuit including a first patient access; said blood circulation circuit also including a blood return circuit for conveying blood from said blood outlet back into the patient, said blood return circuit including a second patient access separate from said first patient access;

one or more pumps operably associated with said blood circulation circuit for circulating blood through said blood circulation circuit in a direction generally from said first access to said second access;

bypass means fluidly connecting said blood removal circuit to said blood return circuit for allowing blood circulated by said pump to bypass said dialyzer, said bypass means being effective to reduce blood-side tensioning of said dialyzer membranes whereby effective mixing of said sorbent suspension is maintained; and a heat exchanger operably associated with said blood circulation circuit and effective to heat blood circulating in said blood circulation circuit.

7. The apparatus of claim 6 wherein said pump is a centrifugal pump.

8. The apparatus of claim 7 wherein said pump is operably associated with said blood removal circuit.

9. The apparatus of claim 8 wherein the dialyzer is a plate dialyzer.

10. The apparatus of claim 6 and also comprising a heater in said dialysate circuit effective to heat said sorbent suspension to a temperature of at least about 40° C.

* * * * *

UNITED STATES PATENT AND TRADEMARK OFFICE
CERTIFICATE OF CORRECTION

PATENT NO. : 6,156,007         Page 1 of 1
DATED : December 5, 2000
INVENTOR(S) : Stephen R. Ash It is certified that error appears in the above-identified patent and that said Letters Patent is hereby corrected as shown below:

Title page,
Item [63], Related U.S. Application Data,
Line 3, "07/940,646" should read -- 07/940,546 --.

Item [57], ABSTRACT,
Line 4, "with the a blood" should read -- with a blood --.

Item [56], References Cited, OTHER PUBLICATIONS,
Line 6, first entry, "*Eight*" should read -- *Eighth* --.
Line 3, third entry, "Granlick" should read -- Gralnick --.
Line 1, second page, "Moxen" should read -- Mozen --.
Line 12, second page, "Neey" should read -- Neely --.
Line 3, second page, "Natual" should read -- Natural --.

Column 1,
Line 8, "5,354,227" should read -- 5,354,277 --.

Column 6,
Line 60, "more complicated that" should read -- more complicated than --.

Column 13,
Line 24, "temperature at 44°C" should read -- temperature is 44°C --.

Column 19, claim 4,
Line 5, "of claim 2" should read -- of claim 3 --.

Signed and Sealed this

Fifth Day of March, 2002

*Attest:*

JAMES E. ROGAN
*Attesting Officer*   *Director of the United States Patent and Trademark Office*